US005646015A

United States Patent [19]
Wong et al.

[11] Patent Number: 5,646,015
[45] Date of Patent: *Jul. 8, 1997

[54] EXCRETION OF HETEROLOGOUS PROTEINS FROM E. COLI

[75] Inventors: W. K. Raymond Wong, Mississauga, Canada; Margaret L. Sutherland, Cambridge, United Kingdom

[73] Assignee: Astra AB, Sodertalje, Sweden

[*] Notice: The term of this patent shall not extend beyond the expiration date of Pat. No. 5,223,407.

[21] Appl. No.: 439,132

[22] Filed: May 11, 1995

Related U.S. Application Data

[60] Continuation of Ser. No. 28,144, Mar. 9, 1993, abandoned, which is a division of Ser. No. 395,797, Aug. 18, 1989, Pat. No. 5,223,407, which is a continuation-in-part of Ser. No. 239,145, Aug. 31, 1988, abandoned.

[51] Int. Cl.$^6$ ............................. C12N 15/16; C12N 15/70
[52] U.S. Cl. ............................. 435/69.4; 435/252.33
[58] Field of Search ............................ 435/69.1–69.52, 435/172.3, 320.1, 252.33, 252.3; 935/40, 41, 48; 536/23.2, 23.4, 23.5–23.52

[56] References Cited

U.S. PATENT DOCUMENTS

| 4,595,658 | 6/1986 | Zinder et al. | 435/69.1 |
| 4,994,559 | 2/1991 | Moscatelli et al. | 530/399 |
| 5,223,407 | 6/1993 | Wong et al. | 435/69.1 |

FOREIGN PATENT DOCUMENTS

| 140864 | 8/1985 | European Pat. Off. . |
| 177343 | 9/1986 | European Pat. Off. . |
| 86/03519 | 6/1986 | WIPO . |
| 88/00206 | 1/1988 | WIPO . |
| 88/03171 | 5/1988 | WIPO . |

OTHER PUBLICATIONS

Miller et al, Gene 24: 309 (1983).
Bittner et al, Gene 15: 319 (1981).
Blight et al, TIB Tech 12: 450 (1994).
Watson, "Compilation of Published Signal Sequences", *Nucleic Acids Research*, vol. 12:5145–5164, (1984).
Oka et al, "Synthesis and Secretion of Human Epidermal Growth Factor by *Escherichia coli*", *Proc. Natl. Acad. Sci. USA*, vol. 82:7212–7216 (1985).
Hsiung et al, "High–Level Expression, Effecient Secretion and Folding of Human Growth Hormone in *Excherichia coli*", *Biotechnology*, vol. 4:991–995, (1986).
Guo et al, "Leakage of Cellulomonas Fimi Cellulases From *Excherichia coli*", *FEMS Microbiol. Lett.*, vol. 49:279–283, (1988).
Wosnick et al, "Rapid Construction of Large Synthetic Genes: Total Chemical Synthesis of Two Different Versions of the Bovine Prochymosin Gene," *Gene*, vol. 60:115–127, (1987).
Kunkel, "Rapid And Efficient Site–Specific Mutagenesis Without Phenotypic Selection", *Proc. Natl. Acad. Sci. USA*, vol. 82:488–492, (1985).
Hendy et al, "Nucleotide Sequences of Cloned cDNAs Encoding Human Preproparathyroid Hormone", *Proc. Natl. Acad. Sci. USA*, vol. 78:7365–7369, (1981).
Bell et al, "Human Epidermal Growth Factor Precursor: cDNA Sequence, Expression in Vitro and Gene Organization", *Nucleic Acids Research*, vol. 14:8427–8446, (1986).
Hirano et al, "Complementary DNA for a Novel Human Interleukin (BSF–2) That Induces B Lymphocytes to Produce Immunoglobulin", *Nature*, vol. 324:73–76, (1986).
Kabayashi et al, "Excretion of the Penicillinase of an Alkalophilic Bacillus sp. Through the *Exchericia coli* Outer Membrane is Caused By Insertional Activation of the Kil Gee in Plasmid pMB9", *J. Bacteriol.*, 728–732,(1986).
Mackman et al, "Release of a Chimeric Protein Into the Medium From *Escherichia coli* Using the C–Terminal Secretion Signal of Haemolysin", *EMBO J.*, vol. 6:2835–2841, (1987)
Nagahari et al, "Secretion Into the Culture Medium of a Foreign Gene Product From *Escherichia coli*: Use of the ompF Gene For Secretion of Human B–Endorphin", *EMBO J.*, vol. 4:3589–3592, (1985).
Maddon et al, "The Isolation and Nucleotide Sequence of a cDNA Encoding the T Cell Surface Protein T4: A New Member of the Immunoglobulin Gene Family", *Cell*, vol. 42:93–104, (1985).
Wong et al, "Wood Hydrolysis by Cellulomonas Fimi Endoglucanase and Exoglucanase Coexpressed as Secreted Enzymes in Saccharomyces Cerevisiae", *Bio/Tecnology*, vol. 6:713–719, (1988).
Koj et al, "A simple Bioassay for Monocyte–Derived Hepatocyte Stimulating Factor: Increased Synthesis of $a_2$–Macroglobulin and Reduced Synthesis of Albumin by Cultured Rat Hepatocytes", *J. Immunol.*, vol. 76:317–327, (1986).
Rosenberg et al, "Regulatory Sequences Involved in the Promotion and Termination of RNA Transcription", *Ann. Rev. Genet.*, vol. 13:319–353, (1979).
Bagdasarian et al, "Activity of the Hybrid trp–lac(tac) Promoter of *Escherichia coli* in Pseudomonas Putida. Construction of Broad–Host–Range, Controlled–Expression Vectors", *Gene*, vol. 26:273–282, (1983).

(List continued on next page.)

*Primary Examiner*—James Martinell
*Attorney, Agent, or Firm*—Foley & Lardner

[57] ABSTRACT

A recombinant DNA construct, useful for obtaining excretion from *E. coli* of a heterologous protein, comprises a coding region in which DNA coding for the heterologous protein in coupled in reading frame with DNA coding for the OmpA signal peptide, to enable secretion of the protein into the periplasm; and a control region linked operably with the coding region to enable expression thereof in an *E. coli* host, wherein the control region comprises the tac promoter, the lac operator and a consensus ribosome binding site. With this construct, the excretion of heterologous proteins from *E. coli* can be achieved, consistently and for a wide variety of such proteins, without assistance from carrier proteins or membrane-lytic agent and by using "healthy" hosts rather than mutant strains having defective outer membranes.

20 Claims, 10 Drawing Sheets

OTHER PUBLICATIONS

Miller et al, "Nucleotide Sequence of the Partition Locus of *Escherichia coli* Plasmid pSC101", Gene, vol. 24:309–315, (1983).

Nossal et al, "The Releae of Enzymes by Osmotic Shock From *Escherichia coli* in Exponential Phase", *J. Biol. Chem.*, vol. 241:3055–3062, (1966).

Van Kimmenade et al., "Secretion Of Murine and Human Intterleukin–2 By *Escherichia coli*", Journal of Biotechnology, vol. 11:11–24, (1989).

Rabbani et al, "Recombinant Human Parathyroid Hormone Synthesized In *Escherichia coli*, The Journal of Biological Chemistry", vol. 263:1307–1313, (1988).

Bittner et al., Gene 15:319 (1981).

2

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 249 base pairs
( B ) TYPE: nucleic acid
( C ) STRANDEDNESS: double
( D ) TOPOLOGY: linear ( x i ) SEQUENCE DESCRIPTION: SEQ ID NO:1:

```
GGGGTACCTT  ACTCCCCATC  CCCCTGTTGA  CAATTAATCA  TCGGCTCGTA  TAATGTGTGG    60

AATTGTGAGC  GGATAACAAT  TTCACACAGG  AGGAAAAAAT  TATGAAAAAG  ACAGCTATCG   120

CGATTGCAGT  GGCACTGGCT  GGTTTCGCTA  CCGTAGCGCA  GGCCGCATGC  TCTAGATATC   180

GATCGCGAGG  CCTGCAGGCT  TAATTAATTA  AGCAGCCCGC  CTAATGAGCG  GGCTTTTTTT   240

TAAGCTTGG                                                               249
```

( 2 ) INFORMATION FOR SEQ ID NO:2:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( x i ) SEQUENCE DESCRIPTION: SEQ ID NO:2:

```
GAATTCATGT  CT                                                           12
```

( 2 ) INFORMATION FOR SEQ ID NO:3:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( x i ) SEQUENCE DESCRIPTION: SEQ ID NO:3:

```
GAATCCATGT CT                                                                    12
```

(2) INFORMATION FOR SEQ ID NO:4:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (x i) SEQUENCE DESCRIPTION: SEQ ID NO:4:

```
GCATGCTCTA GAAAT                                                                 15
```

(2) INFORMATION FOR SEQ ID NO:5:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (x i) SEQUENCE DESCRIPTION: SEQ ID NO:5:

```
GCATGCTCTA GATATCGATC GAGCTTACCT GCCATGCCA                                       39
```

EXCRETION OF HETEROLOGOUS PROTEINS FROM E. COLI

This application is a continuation of application Ser. No. 08/028,114, filed Mar. 9, 1993, now abandoned, which is a division of Ser. No. 07/395,797 filed Aug. 18, 1989, now U.S. Pat. No. 5,223,407, which is a continuation-in-part of Ser. No. 07/239,145 filed Aug. 31, 1988, now abandoned.

This invention relates to the art of genetic engineering as applied to *Escherichia coli*. More particularly, the invention relates to genetically engineered *E. coli* cells that excrete heterologous proteins to the medium in which those cells are cultured.

BACKGROUND TO THE INVENTION

Techniques are now well established for directing *E. coli*-produced heterologous proteins across the inner membrane of the *E. coli* cell envelope, into a space between the inner and the outer membrane known as the periplasm. It has been shown that when a protein is expressed as a fusion protein, having an *E. coli*-recognized peptide or "signal peptide" attached to its N-terminus, the desired protein is secreted into the periplasm (see EP 177,343 Genentech Inc.). Several such signal peptides have now been identified by amino acid and DNA sequence (see Watson, M. Nucleic Acids Research, Vol 12, No. 13, 1984, pp. 5145–5164) and have been used successfully to direct heterologous proteins into the *E. coli* periplasm (see Oka et al, Proc. Natl. Acad. Sci. U.S.A., Vol 82, pp 7212–7216, November 1985 in which human epidermal growth factor (hEGF) was fused with the signal peptide of *E. coli* alkaline phosphatase to direct mature EGF into the *E. coli* periplasm; and see Hsiung et al, Biotechnology, Vol 4, November 1986, pp 991–995 where human growth hormone was directed into the *E. coli* periplasm using the signal peptide of outer membrane protein A (ompA) of *E. coli*).

While these periplasmic proteins are often described as "secreted" it should be understood that they are contained intracellularly by the outer membrane and, because they are not available in the medium, can be recovered only once the outer membrane is either disrupted or "permeabilized" to release the periplasmic components.

To facilitate the protein recovery process it is preferable that the protein accumulates in the culture medium during culturing of the protein-producing *E. coli* host, since there are relatively fewer contaminants and the protein can be recovered without damaging its cellular source. There have been various attempts at developing such a system, for excreting proteins to the medium, all of which include some tactic for overcoming the integrity of the outer membrane barrier.

One approach generally involves genetically engineering *E. coli* to co-express the desired protein in secretable form (bearing a signal peptide) together with a lyric protein which affects outer membrane integrity to the extent that it becomes permeable or "leaky" (see U.S. Pat. No. 4,595,658 in which the gene III product of the fI phage is used as the permeabilizing agent; Kobayashi et al, J. Bacteriol. June 1986, pp 728–732 in which activation of the cryptic kil protein is used; and see EP 140,864 in which a temperature sensitive lysogen is used). In these methods, careful control of lyric product expression is required to maintain host viability. Moreover, co-expression per se can be an energy drain on the host, reducing yield of the desired protein and reducing host cell biomass.

In another approach, the desired protein is expressed as a chimeric protein, in which the desired protein is fused to a carrier protein. The carrier proteins typically used are those naturally produced *E. coli* proteins, or fragments thereof, which are capable of being excreted (hemolysin) or which are bound to the outer membrane (ompF). For example, Mackman et al found that ompF, without its signal peptide, could be dragged through the *E. coli* envelope to the medium when fused with a C-terminal portion of hemolysin (EMBO J. Vol 6, No. 9, pp. 2835–2841, 1987). Nagahari et al found that human β-endorphin was released to the medium when fused with at least a portion of the *E. coli* ompF protein (EMBO J. Vol 4, No. 13A, pp. 3589–3592, 1985). To recover proteins produced by such techniques, however, the desired protein must be cleaved from the carrier protein, which makes isolation difficult.

Yet another approach makes use of *E. coli* strains in which the integrity of the outer membrane has been compromised at the genetic level. Such strains, known as "leaky" hosts, are incapable of retaining periplasmic proteins. In practise, these strains are difficult to maintain in a viable condition without stringent control of environmental conditions.

It is an object of the present invention to provide a method enabling heterologous proteins to be excreted to the culture medium in which the protein-producing *E. coli* host is grown.

It is an object of the present invention to provide a DNA vector enabling excretion from *E. coli* of a heterologous protein encoded thereon.

It is a further object of the invention to provide an *E. coli* strain that has been genetically engineered to express a desired heterologous protein which is excreted to the medium in which the *E. coli* strain is cultured.

It is an overall object of the present invention to facilitate recovery of *E. coli*-produced, heterologous proteins by enabling accumulation of those proteins in the *E. coil.* culture medium.

SUMMARY OF THE INVENTION

It has now been found that the excretion of heterologous proteins from *E. coli* hosts can be achieved, consistently and for a wide variety of heterologous proteins, without assistance from carrier proteins or membrane-lyric agents and by using "healthy" hosts rather than mutant strains having defective outer membranes. More particularly it has been found that heterologous proteins expressed from DNA vectors as herein described are excreted directly into the culture medium and are recoverable therefrom in relatively significant yields.

In accordance with one aspect of the present invention, there is provided a recombinant DNA construct useful for obtaining excretion from *E. coli* of a heterologous protein, comprising a coding region in which DNA coding for a heterologous protein is coupled in reading frame with DNA coding for the ompA signal peptide to enable secretion of the protein to the periplasm; and a control region linked operably with the coding region to enable expression thereof wherein the control region comprises the tac promoter, the lac operator and a consensus ribosome binding site. The recombinant DNA construct is preferably incorporated on a vector, to form an *E. coli* excretion vector useful for creating *E. coli* transformants that excrete heterologous proteins.

In accordance with another aspect of the invention, there is provided an *E. coli* host which excretes a heterologous protein into the medium in which the host is cultured as a result of having been transformed by the recombinant DNA construct of the invention, as characterized above. According to preferred embodiments of this aspect of the invention, E. coli cells are provided that are capable of excreting mammalian proteins or fragments thereof.

According to another aspect of the invention, there is provided a method for producing a heterologous protein which comprises culturing a transformed E. coli strain of the invention in a culturing medium and then recovering the heterologous protein directly from the medium in which the strain has been cultured. In particularly preferred embodiments of this aspect of the invention, the method is applied for the production of such human proteins as parathyroid hormone (PTH), epidermal growth factor (EGF), interleukin-6 (IL-6) and soluble CD4 (the extracellular domain of a T-cell membrane protein).

Using the system herein described, relatively large amounts of heterologous protein are excreted to the culture medium, thereby providing not only for a simplified protein recovery process but also providing the protein in significant yield. The present excretion system is unencumbered by requirements known in other prior art systems: excretion resulting from the present system is direct, occurs in the absence of cell lysis, and is consistently reproducible within non-restrictive parameters hereinafter described.

DETAILED DESCRIPTION OF THE INVENTION AND PREFERRED EMBODIMENTS

This invention relates to a system for producing heterologous proteins in the host E. coli, whereby such proteins are excreted to the medium in which the host is cultured.

By the term "heterologous protein" is meant a protein which, although not naturally produced by E. coli, is expressed by this host when suitably transformed with DNA coding for the protein, such as genomic DNA, cDNA and synthetic DNA. Among the heterologous proteins that may be produced using the system herein described, naturally secreted mammalian proteins including those of human origin are preferred, particularly those protein species having therapeutic value such as growth factors, lymphokines, hormones, interferons, enzymes and the like. Moreover, there appears to be no restrictive limit on the size of protein that can be excreted using the present system, although proteins exceeding about 100 kD may be excreted at lower than preferred levels. Most suitably, proteins produced using the present system are those proteins having a molecular weight in the range from about 5 to 50 kD.

It will be appreciated as well that, although the production of mature proteins may be preferred, in order to allow direct isolation from the medium of the authentic form of the protein, hybrid proteins may also be produced and excreted in accordance with the invention as may fragments of the authentic protein. Hybrid proteins may include authentic proteins bearing additional amino acid residues which enhance, or at least do not detract from, the biological activity of the authentic protein. Fragments of authentic proteins may include biologically active domains of the authentic protein.

Figure 1:
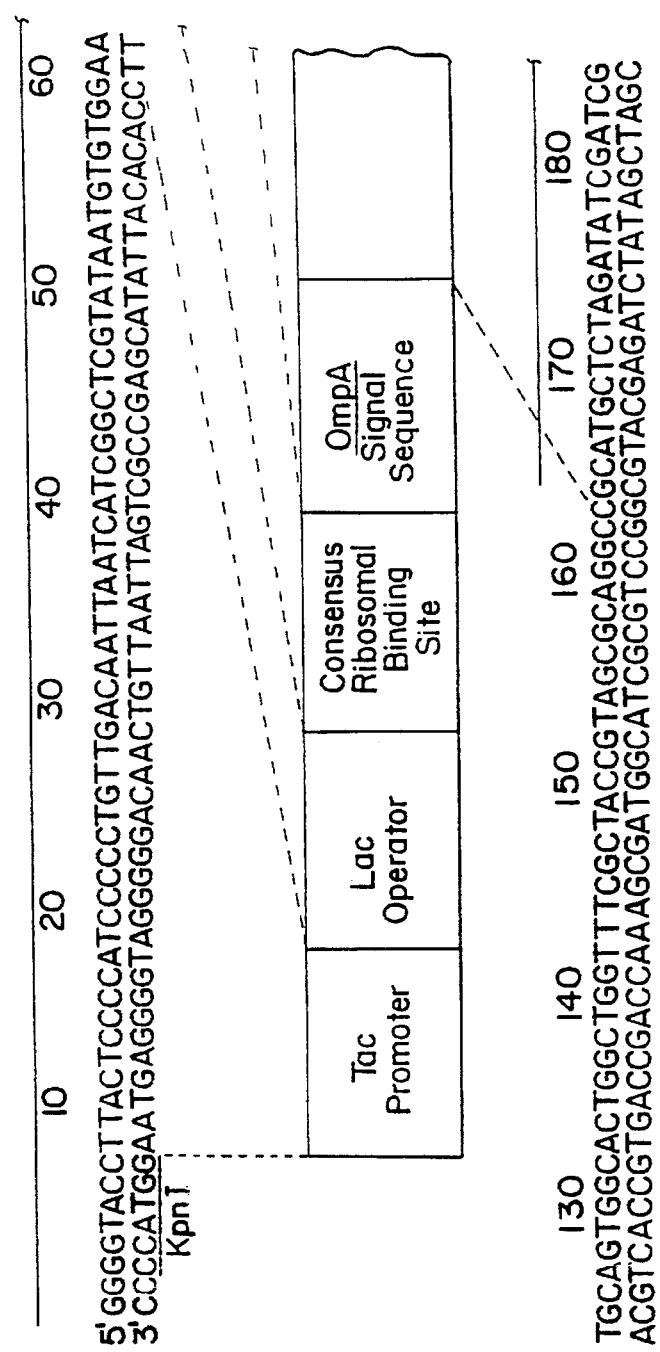
FIG. 1 provides the nucleotide sequence (SEQ ID NO:1) and a schematic representation of a recombinant DNA construct useful in accordance with the invention. Solid, horizontal lines identify the four synthetic oligonucleotides used to assemble the construct.
Figure 1:
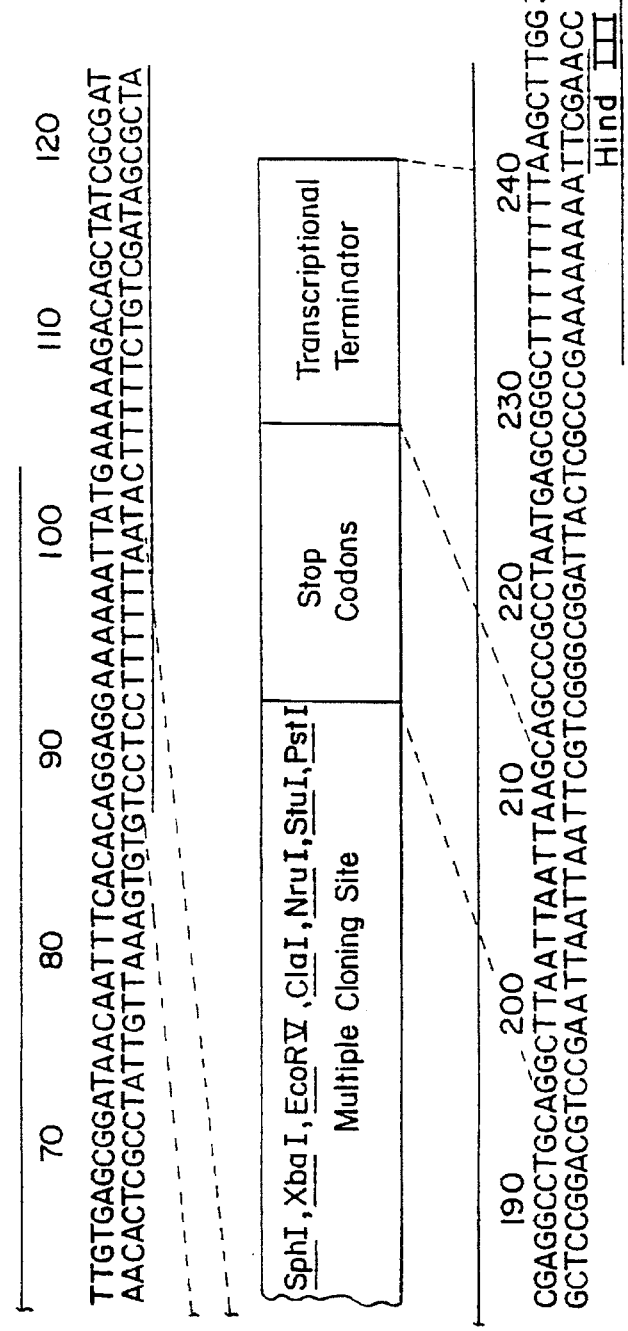

Although originally designed to enable large amounts of heterologous protein to be secreted to the periplasm of an E. coli host, with the full expectation that the protein would accumulate in and require recovery from the periplasm, it was surprisingly found that the DNA construct illustrated in FIG. 1 (SEQ ID NO:1) is capable of causing excretion of heterologous protein to the medium. The components of the construct are, in fact, associated in a manner typical of E. coli secretion vectors. That is, a control region which includes a promoter, operator and ribosome binding site is linked with a coding region having DNA coding for an E. coli-recognized signal peptide located upstream of a multiple cloning site for incorporation of DNA coding for a desired heterologous protein to enable secretion of the heterologous protein to the periplasm. By selecting from among the available components those with superior efficiency, however, constructs have been developed that enable the heterologous protein coded thereon to be excreted to the medium in which the E. coli host is cultured.

The most preferred recombinant DNA construct is illustrated in FIG. 1 (SEQ ID NO:1) to which reference is now made. To produce this construct, the four single-stranded oligonucleotides identified by horizontal lines on FIG. 1 were individually synthesized by the phosphoramidite method. The gel-purified oligonucleotides were then assembled by annealing and gaps were filled in with the aid of DNA sequenase, to provide the double-stranded construct as illustrated. Thus, the construct was prepared using standard gene synthesis methodology, as described for example by Wosnick et al in Gene, Vol 60, pp 115–127, 1987.

As depicted in FIG. 1, the construct comprises the hybrid tac promoter, the lac operator, a consensus ribosome binding site, ompA signal peptide-encoding DNA, a multiple cloning site, translational stop codons in all three reading frames and a transcriptional termination region associated relative to each other according to the nucleotide sequence indicated. The construct illustrated in FIG. 1 incorporates the transcriptional terminator of the E. coli trpA gene, although it will be appreciated that other transcriptional terminators may be employed in its place, such as those asscociated with the thr, his and phe genes of E. coli. Nucleotide sequences of these terminators are provided by Rosenberg and Court in Ann. Rev. Genet., 1979, Vol. 13, 319–355. The construct illustrated in FIG. 1 is provided also with flanking restriction sites for convenient ligation into a suitable E. coli vector, or into phage vectors such as M13mp18, in which sequencing and site-specific mutagenesis may be performed.

To provide for protein excretion, the construct, hereinafter designated simply as Tac, may be incorporated on any of the commercially available *E. coli* vectors to enable it to be introduced and stably maintained in *E. coli*. Although phage vectors can be employed, plasmid vectors are preferred. The pUC series of plasmids are particularly suitable. So that the restriction sites within the multiple cloning site of the Tac cassette remain unique, however, common sites in the selected vector are preferably deleted. Once incorporated on a suitable vector, the resulting plasmid may be amplified in *E. coli* to provide amounts sufficient for subsequent cloning work.

It will be appreciated that DNA coding for the selected heterologous protein is conveniently incorporated on the plasmid within the multiple cloning sites provided thereon, using standard cloning/ligation methods. To incorporate protein-encoding DNA into the construct, the cloning site and cloning technique are selected to enable the protein-encoding DNA to be incorporated in reading frame with the ompA signal-peptide encoding DNA. To enable the ompA signal peptide and heterologous protein to be fused directly when expressed, without intervening amino acid residues that are superfluous, the fusion junction may be tailored by site-specific mutagenesis using, for example, the technique generally described by Kunkel, Proc. Natl. Acad. Sci. U.S.A., Vol 82, pp. 488-492, 1985. The same technique may, also be used to remove portions of the heterologous protein-encoding DNA, for example to enable fragments of the protein to be expressed.

Once DNA coding for the desired heterologous protein is incorporated on the excretion vector, a selected *E. coli* strain is transformed therewith using standard methods.

*E. coli* strains useful as hosts include commercially available "healthy" strains. Strains characterizable as healthy are those strains which, when cultured under normal conditions, do not release periplasmic proteins or cytoplasmic proteins to the medium in which they are grown. For example, when cultured in standard growth medium, the medium in which suitable strains are grown should not contain detectable amounts of either β-galactosidase or β-lactamase (for strains that naturally produce these proteins as cytoplasmic and periplasmic proteins, respectively). Because the Tac construct (FIG. 1) from which the desired heterologous protein is expressed makes use of the tac promoter and lac operator, as described in more detail hereinafter, the transformed host strain should be capable of expressing, preferably over-producing, the lacI product so that expression of the heterologous protein can be regulated.

The need for lacI overproduction by the *E. coli* transformant can be met, according to one embodiment of the invention, by using *E. coli* hosts that already harbour the lacI$^q$ gene responsible for overproduction of the lacI product. LacI over-producing strains that may be employed as host include the JM series of *E. coli* strains available from Clontech Laboratories Inc., California, USA. Specific host strains suitable for use include JM 103 and JM105 (JM 109, a recA host should be avoided since it may be subject to lysis). Preferred for use herein is the strain JM 101.

The need for lacI overproduction in the transformant may alternatively be met by incorporating the lacI$_q$ gene on the Tac excretion vector. Since, in this situation, the over-production of lacI is mediated by the Tac excretion vector any of a variety of commercially available *E. coli* strains may be employed as host, including such strains as DH1, RR1, C600, CMK603 and EB505. The lacI$^q$ gene to be incorporated on the Tac excretion vector may be obtained as a 1.2 kb HindIII fragment of plasmid pMMB22 (described by Bagdasarian et al in Gene 26,273-282, 1983) and then incorporated non-disruptively at any site on the plasmid vehicle containing the Tac construct.

To enhance the stability of inheritance of the plasmid from the strain originally transformed to its progeny, a partition element (par) functional in *E. coli* may also be incorporated on the Tac excretion vector. The nature and location of one such par element, contained on *E. coli* plasmid pSC101, is described by Miller et al in Gene 24, 309-315, 1983. This par element may be liberated from pSC101 as a 380 bp HincII/AvaI fragment and then cloned into a suitable site on the Tac excretion vector.

Following transformation, *E. coli* strains harbouring the excretion vector are cultured in a culturing medium most appropriate for the selected host. Generally, LB broth or 2YT medium (yeast extract/tryptone)can be used to culture those strains herein preferred. Selective pressure should be maintained by providing a metabolite required for survival of the transformant. When pUC-based excretion vectors are used, for example, the medium should contain ampicillin. Ampicillin concentrations of around 70 ug/ml are suitable.

The tac promoter on the construct is regulatable, as mentioned above, through binding of the lacI gene product to the lac operator located adjacent the tac promoter. Binding of lacI product represses the tac promoter, lowering expression levels of coding DNA under its control. To raise expression levels, the chemical IPTG (isopropyl-β-D-thiogalactopyranoside), which binds the lacI product and de-represses the tac promoter, is typically added to the culture medium to raise expression levels, in this circumstance. In accordance with a preferred embodiment of the invention, transformants are cultured in the absence of IPTG. It has been found that yield of excreted protein is not significantly different, and can actually be enhanced when IPTG is not used in the culture medium. Alternatively, IPTG may be added to the medium, preferably when the cells have reached early log growth phase.

Whereas expression from the tac promoter is known to be more efficient at around 37° C., it has been found that lower temperatures can be used without significant yield sacrifice. In accordance with a preferred embodiment of the invention, transformants are cultured at around 30° C. i.e. 28°-32° C. An advantage of working at the lower temperature is, of course, enhanced stability of protein and plasmid copy number.

To determine the optimum time period for which cultures should be grown to realize maximum yield of excreted protein, trials can be conducted and excreted protein assayed in a time-course experiment. In general, it is possible, with the present system, to recover reasonable yields of protein once cells reach early-log phase, although greater amounts of protein can be expected to accumulate in the medium within about 4-10 hours thereafter.

Excretion of the protein to the culture medium greatly facilitates recovery and isolation of the protein. The culture medium can be siphoned from the bioreactor if desired, provided that fresh nutrients are returned to the system. Protein contained in the spent medium can be isolated using biochemical techniques that reflect the nature of the protein in terms of its molecular size, net charge, isoelectric point, etc. The medium may be concentrated first such as by lyophilization. Further, when antibodies are available or a natural ligand for the protein is available, affinity columns may be used.

Specific embodiments of the invention are now exemplified with reference to the drawings.

EXAMPLE 1—Construction of E. coli excretion vectors

Figure 2:
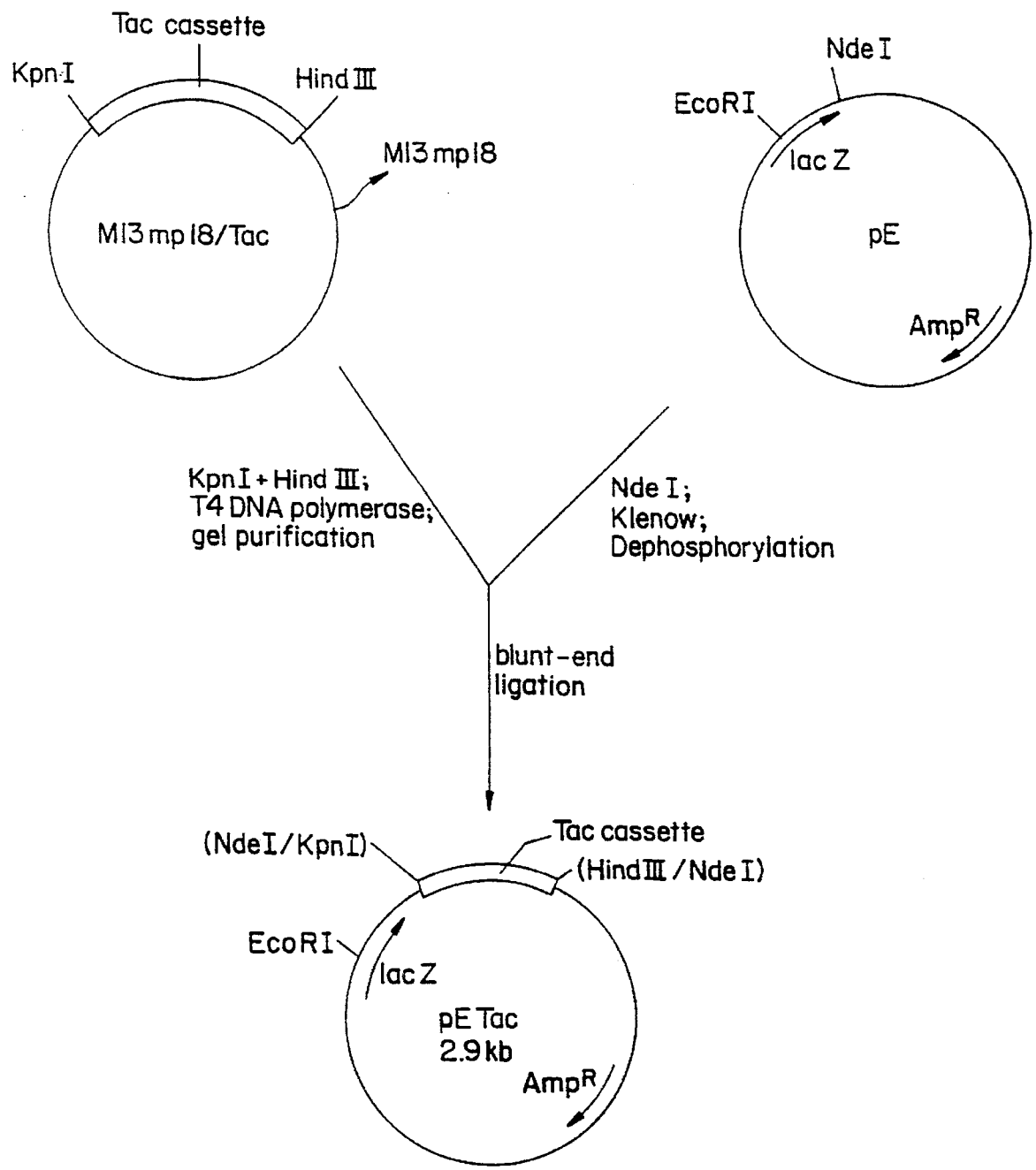
FIG. 2 illustrates the incorporation of the Tac construct into a derivative of the plasmid pUC18, designated pE, to form the plasmid pETac.

Two excretion vectors were constructed, by incorporating the Tac construct illustrated in FIG. 1 and prepared as previously described, on E. coli plasmids containing an origin of replication and a selectable marker. One plasmid vector, designated pETac and shown in FIG. 2, was constructed by incorporating the Tac construct into the NdeI site of plasmid pE, a variant of pUC18 lacking the multiple cloning sites, except EcoRI.

Figure 3:
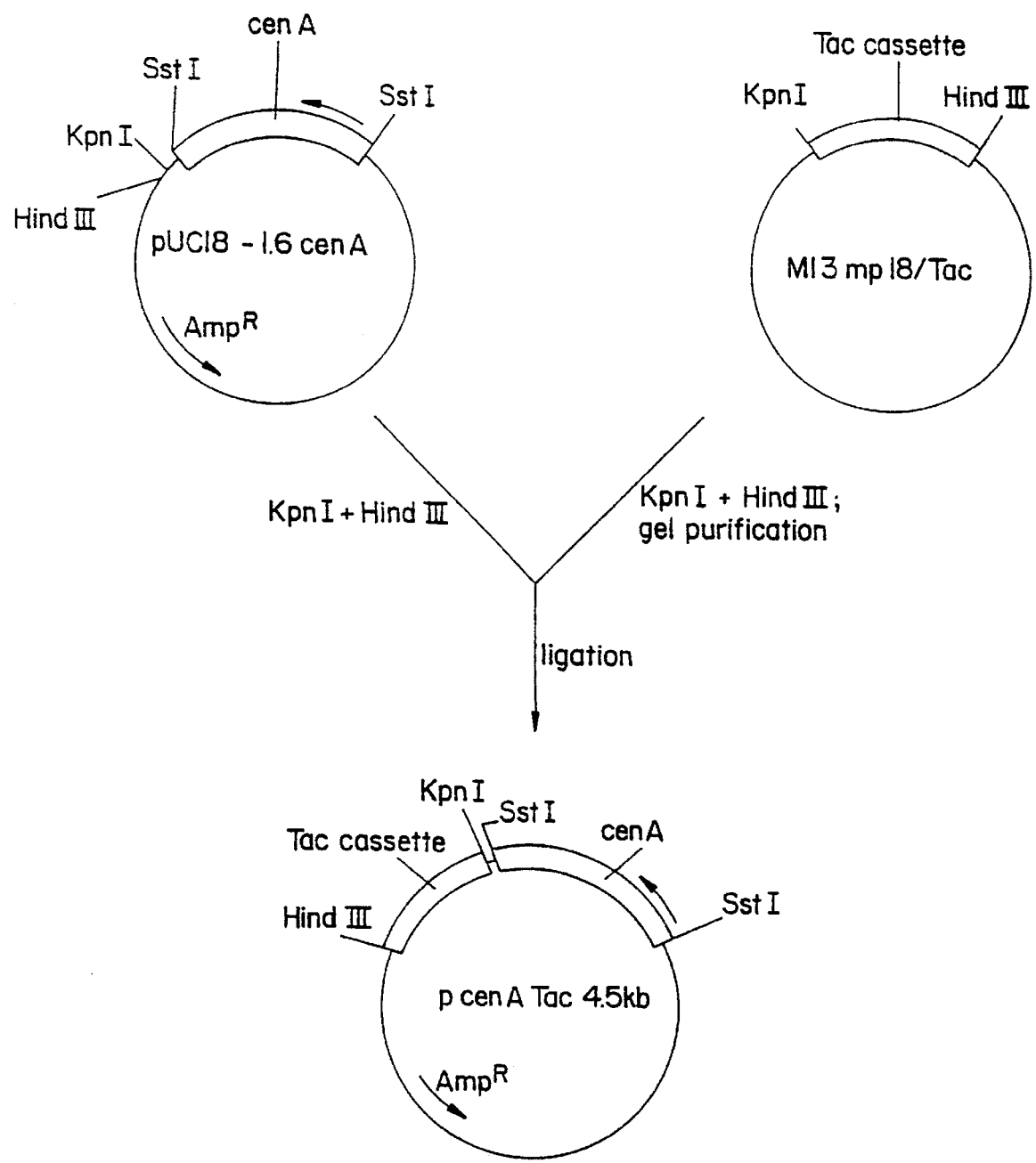
FIG. 3 illustrates construction of a Tac-containing plasmid which also incorporates the C. fimi cenA gene, to form pcenATac.

A second plasmid vector, designated pcenATac was formed as illustrated in FIG. 3 by incorporating the Tac construct between the KpnI/HindIII sites on plasmid pUC 18–1.6 cenA described by Guo et al., FEMS Microbiol. Lett. Vol. 49, pp. 279–283, 1988 which is herein incorporated by reference. The cenA portion of pUC 18–1.6cenA that is also incorporated on excretion vector pcenATac is capable of expressing *Cellulomonas fimi* enctoglucanase. The expressed endoglucanase is excreted when expressed by an E. coli plasmid, as reported by Guo et al., supra, resulting consequentially in the release of E. coli proteins from the periplasm to the culture medium. Based on these prior observations, it was originally postulated that the cenA gene product could be used to facilitate release of heterologous proteins secreted by E. coli to the periplasm. While this may be possible, the evidence presented later in these examples demonstrates that expression of the cenA gene product is not required to obtain excretion of heterologous proteins from an E. coli host when vectors containing the Tac construct are employed. The Tac construct is sufficient per se to excrete a selected heterologous protein encoded thereon. In this light, therefore, it is to be understood that the two excretion vectors described above and used in the examples are substantially the same in the present context. The co-existence of the cenA gene on pcenATac is irrelevant to the proper functioning of the Tac construct, and to the extracellular release of proteins expressed from it.

EXAMPLE 2—Cloning of heterologous protein-encoding DNA

Figure 4:
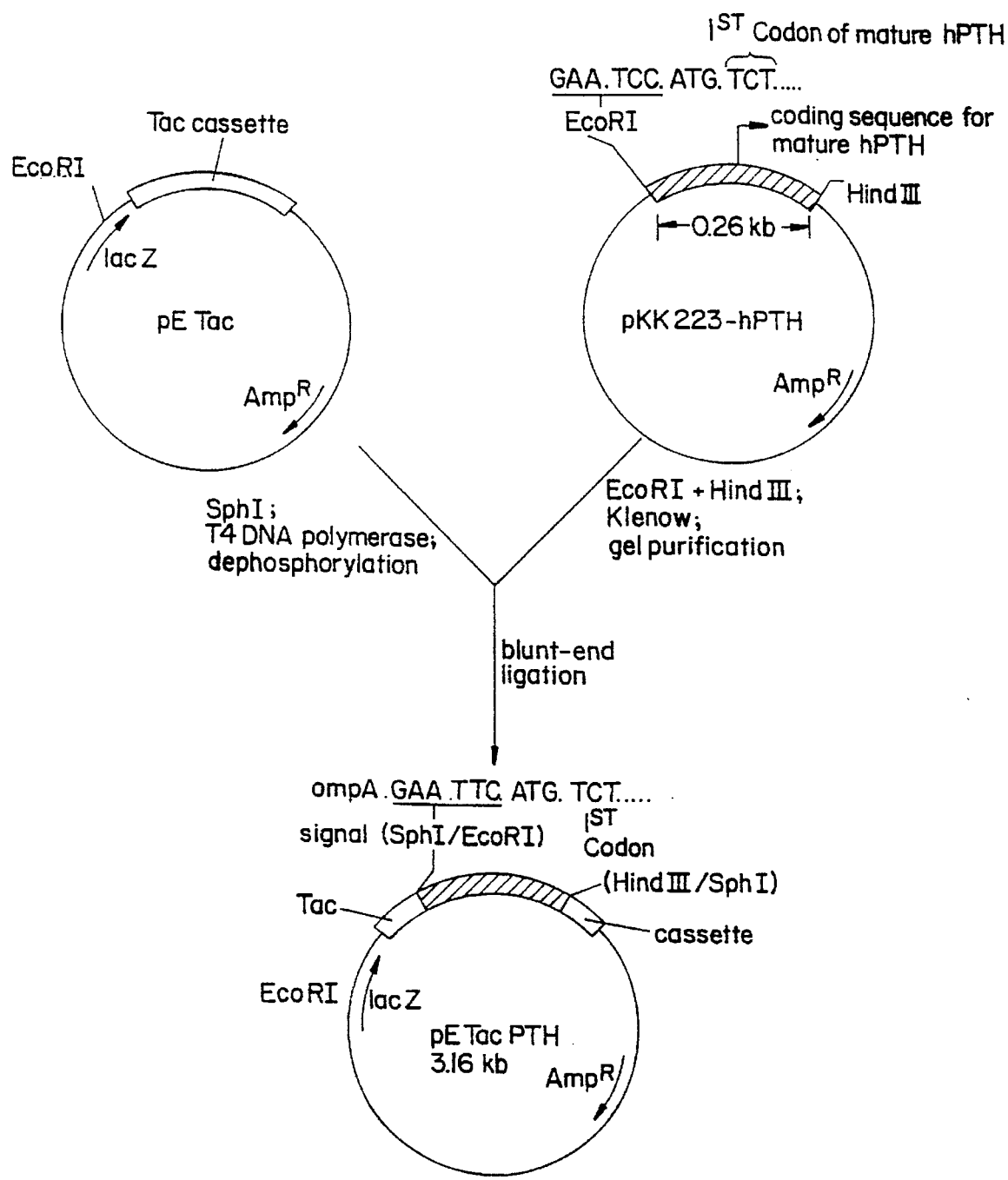
FIG. 4 illustrates the incorporation into pETac of DNA coding for human parathyroid hormone (PTH), to form pETacPTH (SEQ ID NOS 2 and 3 are shown in this Figure)

DNA coding for various proteins of mammalian origin was incorporated into either of the two expression vectors described in Example 1, using strategies indicated in the referenced drawings:

PTH:

In its mature form, PTH is an 84-amino acid peptide that acts in humans to raise blood calcium and increase bone resorption. DNA coding for a PTH analogue, bearing an N-terminal methionine residue was synthesized using the general method described by Wosnick et al, supra, and according to the nucleotide sequence published by Hendy et at., Proc. Natl. Acad. Sci. U.S.A., Vol. 78 pp. 7365–7369, 1981. As indicated in FIG. 4, the synthetic Met PTH-encoding DNA was obtained as an EcoRI/HindIII fragment from plasmid pKK223-PTH and cloned, by blunt-end ligation, into the SphI site of excretion vector pETac. in the manner outlined in the drawing, to form plasmid pETacPTH. In the resulting plasmid, two artifactual amino acid residues are encoded between the ompA signal peptide and Met-PTH.

Figure 5:
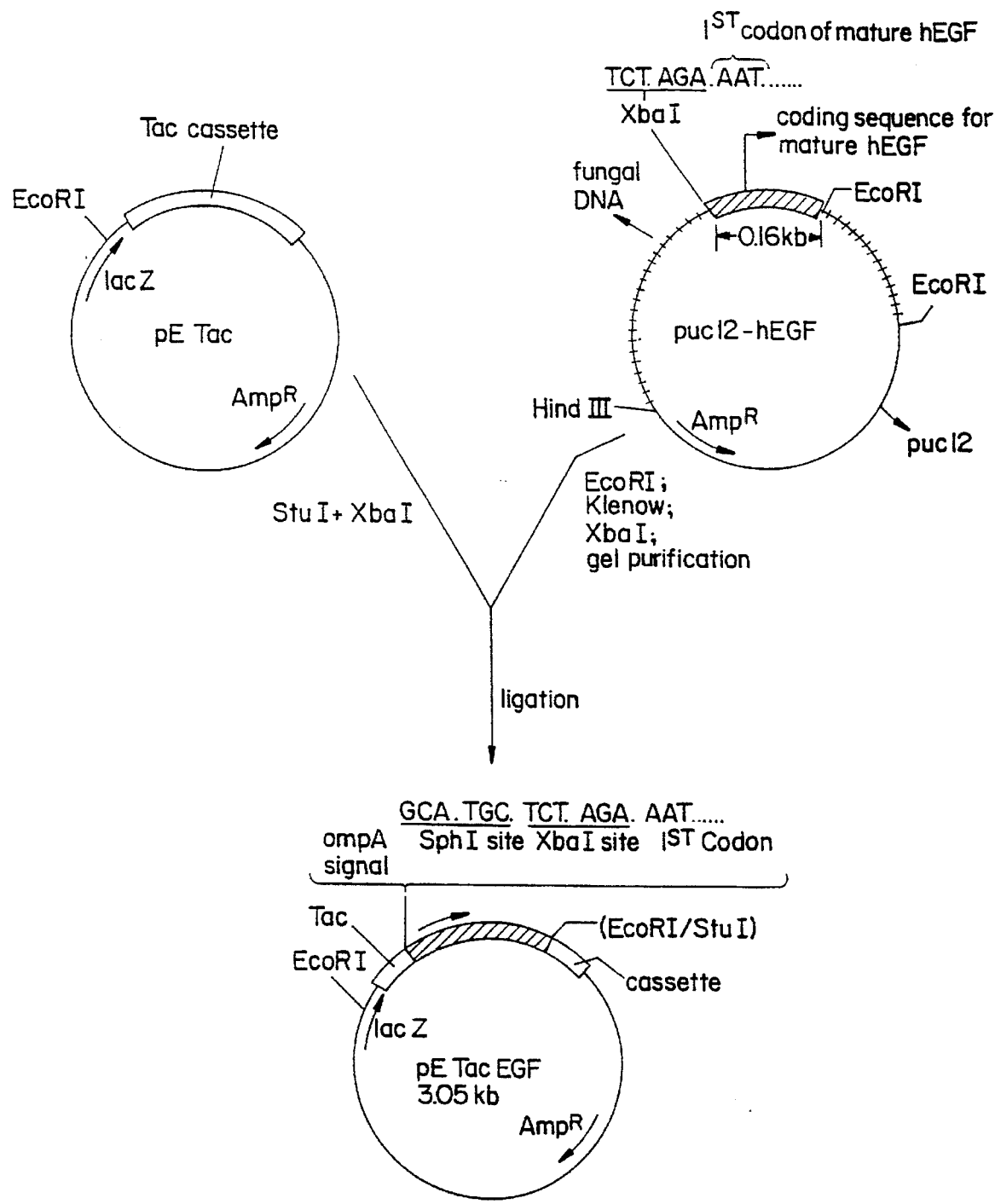
FIG. 5 illustrates the incorporation into pETac of DNA coding for human epidermal growth factor (EGF), to form pETacEGF (SEQ ID NO:4 is shown in this Figure)

EGF:

In its mature form, human EGF is a 53-amino acid peptide having the amino acid sequence indicated by Bell et al., infra. EGF has a variety of therapeutic utilities, including inhibition of gastric acid secretion. Based on the nucleotide sequence published by Bell et al., Nucleic Acids Research, Vol. 14, pp 8427–8446, 1986, an EcoRI/XbaI cassette of EGF-encoding DNA was prepared and cloned previously into pUC12. To clone the EGF-encoding DNA into an E. coli excretion vector, the EGF gene was retrieved from pUC12 and force cloned into StuI/XbaI—digested pETac as indicated in FIG. 5, to produce pETacEGF. In the resulting plasmid, four intervening amino acid residues are encoded between the ompA signal and the N-terminus of EGF (FIG. 5).

Figure 6:
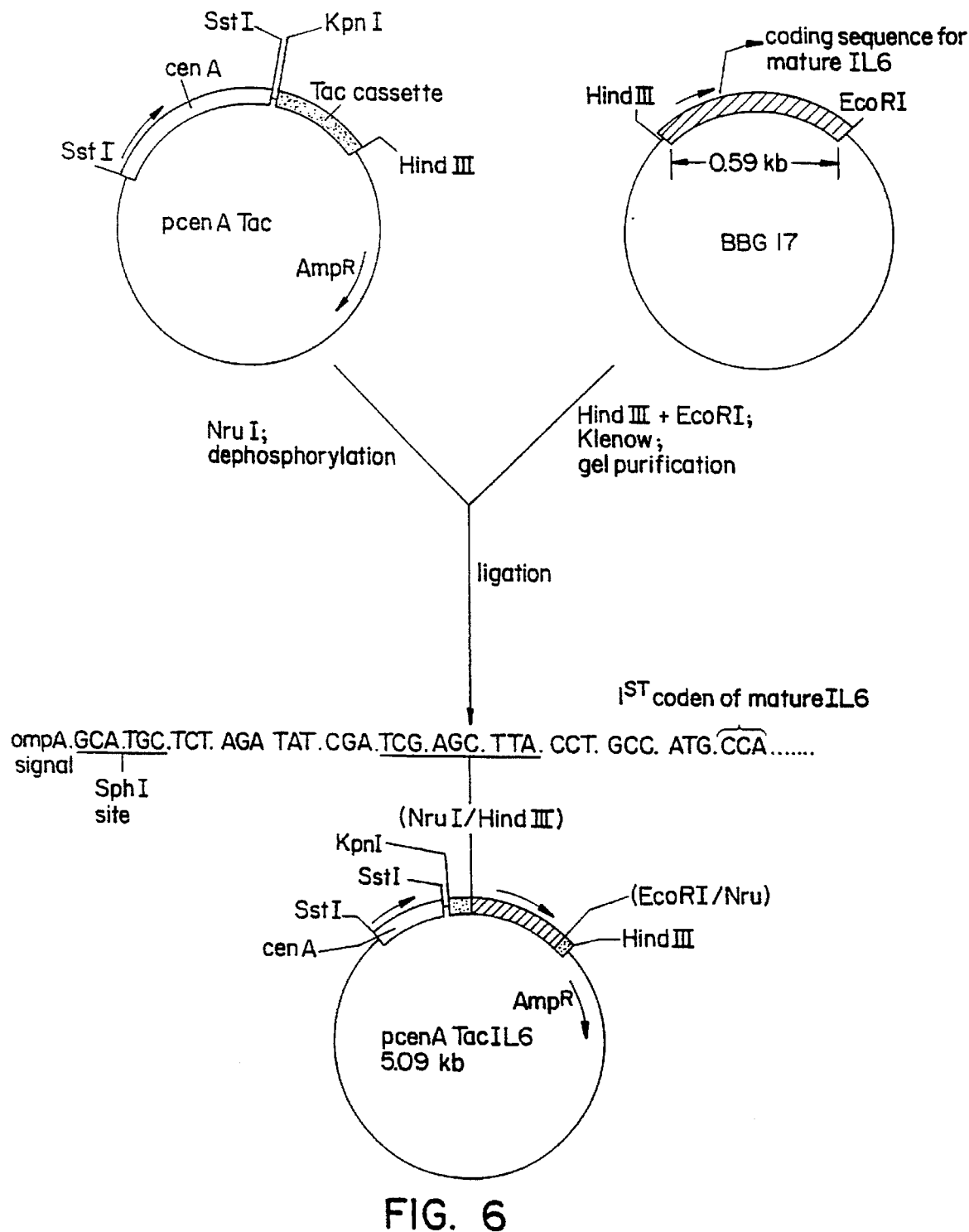
FIG. 6 illustrates incorporation of DNA coding for interleukin-6 (IL-6) into the vector pcenATac to form pcenATacIL6 (SEQ ID NO:5 is shown in this Figure).

INTERLEUKIN-6:

DNA coding for mature interleukin-6, a human protein having numerous and wide ranging physiological activities, was purchased from British Biotechnology Limited (cat #BBG-17). The nucleotide sequence of the IL-6 encoding DNA is as reported by Hirano et al. in Nature, Vol. 324, pp. 73–76, 1986; (see also WO 88/00206). The synthetic DNA construct was then ligated into the NruI site of the Tac construct contained on pcenATac as illustrated in FIG. 6, to form plasmid pcenATacIL6.

Figure 7:
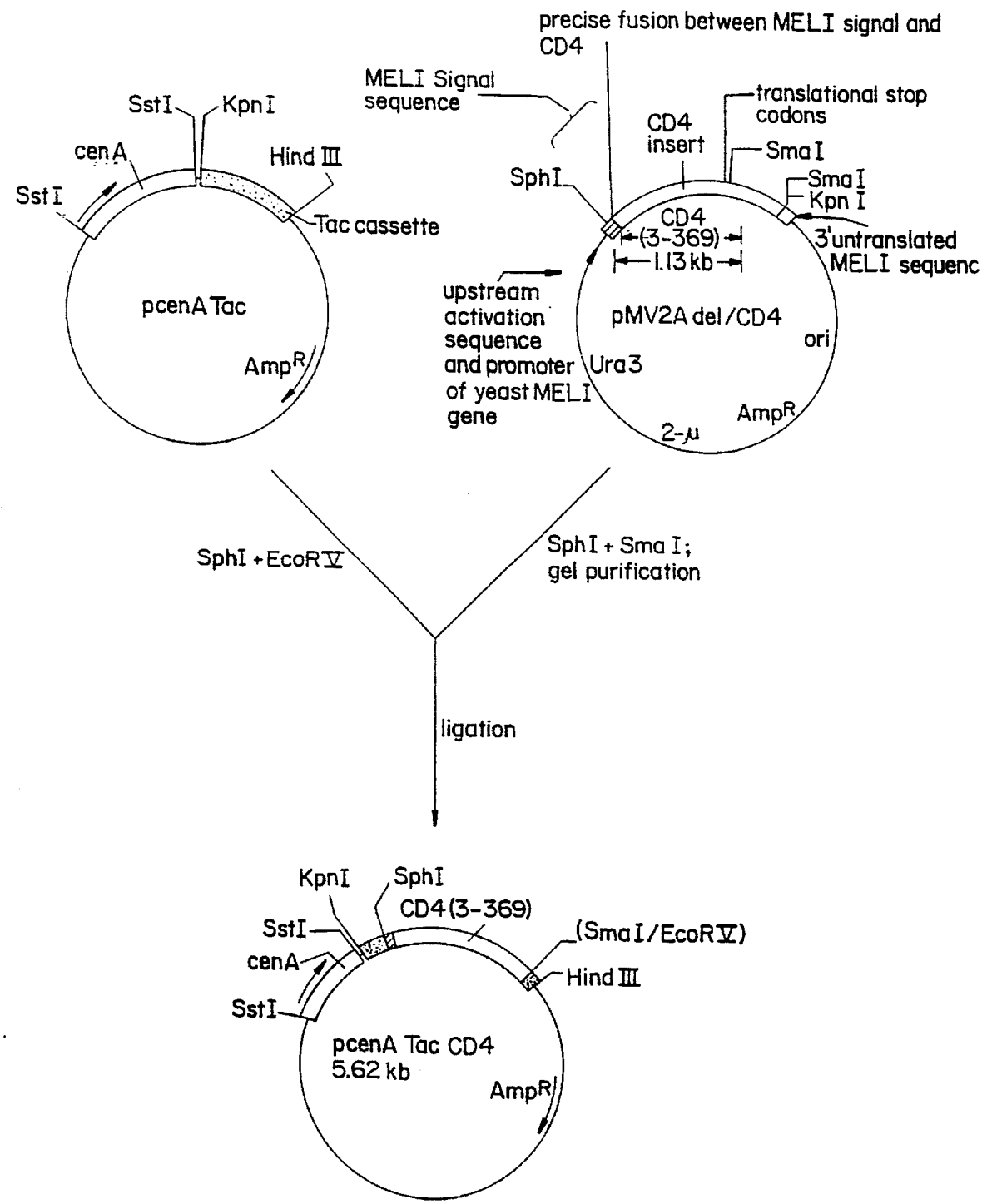
FIG. 7 illustrates incorporation of DNA coding for an extracellular domain of CD4 into plasmid pcenATac to form pcenATacCD4.

EXTRACELLULAR DOMAIN OF CD4:

CD4 is a membrane-bound protein found on human T-cells that is recognized by the AIDS virus and is believed therefore to be involved in the mechanism by which the virus invades these cells. An extracellular domain of CD4 is that portion of the CD4 molecule that extends from the cell membrane into the extracellular environment (this region is also known as "soluble" CD4). DNA coding for the major portion of the CD4 extracellular domain i.e. CD4 3–369, was obtained based on the CD4 amino acid sequence published by Maddon, P. J. et al., Cell, Vol. 42, pp. 93–104, August 1985 and previously cloned into the yeast secretion vector pMV2Adel (Wong et al., Bio/Technology, Vol. 6, pp. 713–719, 1988). The CD4 DNA was liberated from the yeast vector and force cloned into the SphI/EcoRV site on pcenATac, as illustrated in FIG. 7, to form pcenATacCD4. In the resulting plasmid, the ompA signal and CD4 are spaced by nine codons incorporated from the yeast vector source of the CD4 DNA.

In each of the plasmids constructed as described above, DNA coding for a mammalian protein has been incorporated in reading frame with the ompA signal to enable secretion of the protein to the E. coli periplasm. This coding region is, in each case, under the expression control of a control region containing the tac promoter, lac operator and consensus ribosome binding site.

In separate experiments, the plasmids were introduced into E. coil strain JM 101 using standard methods and the transformants cultured according to the protocols indicated more precisely below in order to characterize the location of the heterologous proteins expressed.

EXAMPLE 3—Excretion of Heterologous (Human) Proteins by E. coil

PTH:

JM 101 transformants containing the PTH excretion vector pETacPTH were cultured overnight at 30° C. in LB broth containing ampicillin and then inoculated into fresh medium, with continued culturing at 30° C. until reaching an optical density of 0.3 as measured at OD600 (early log phase). Cultures were then induced (1 mM IPTG). At two hour growth intervals, aliquots of culture were withdrawn and fractionated to produce samples of (1) culture medium to identify excreted products; (2) osmotic shock fluid to identify periplasmic proteins; and (3) sonicated lysate which contains both cytoplasmic and periplasmic proteins and thus provides an indication of the cytoplasmic protein content by comparison with the shock fluid results.

In particular, each fraction was assayed to detect PTH, β-lactamase (a native periplasmic protein) and β-galactosidase (a native cytoplasmic protein) and to measure total protein content. Non-induced cultures were also run for comparison. The results of these trials are provided in Table 1 below:

medium was not a consequence of cell lysis. Further, the appearance of the periplasmic protein β-lactamase, in the medium, indicates that release of PTH from the periplasm is non-specific. The results obtained from similar assays of the non-induced culture i.e. cultures to which IPTG was not added, are consistent with the induced culture assays in those respects noted above, but it should be noted that yield of excreted PTH is not significantly depressed in the absence of IPTG. This is a particularly surprising finding in that IPTG is known to prevent the lacI product from repressing the tac promoter. Accordingly, in the absence of IPTG and the presence of the lacI product, depressed levels of PTH are to be expected. Either method is capable of producing PTH in relatively good yield, with maximum yields being realised about 10 hours after the culture has reached early log phase.

EGF:

*E. coli* JM 101 transformants containing the EGF excretion plasmid pETacEGF were evaluated in substantially the same manner as described above for PTH. The results, as indicated in Table 2 below, mirror those of the PTH transformant:

TABLE 1

Determination of Protein Concentration and Enzymatic Activities in Various Fractions of *E. coli* Culture Expressing hPTH

A Results for Induced Culture

| Hr. After IPTG Induction | Protein Conc.[1] mg/L | | | hPTH Conc.[2] mg/L | | | β-lactamase[3] Activity U/L | | | β-galactosidase[4] Activity U/L | | |
|---|---|---|---|---|---|---|---|---|---|---|---|---|
| at O.D.$_{600}$ = 0.3 | C[5] | P[6] | S[7] | C | P | S | C | P | S | C | P | S |
| 0  | 11  | 2.9  | 21 | 0    | 0    | 1.54 | 3.0 | 0.3 | 4  | 0.68 | Not | |
| 2  | 16  | 3.5  | 21 | 0.13 | 0.1  | 1.0  | 4.0 | 3.4 | 8.5 | 0.18 | Detect- | |
| 4  | 11  | 6.7  | 21 | 0.38 | 0.07 | 2.1  | 8.0 | 2.9 | 16 | 0.68 | able | |
| 6  | 302 | 9.7  | 27 | 1.0  | 0.02 | 2.3  | 1.9 | 4.7 | 28 | 2.28 | | |
| 8  | 208 | 5.8  | 24 | 0.38 | 0.02 | 6.2  | 2.0 | 2.9 | 21 | 3.88 | | |
| 10 | 214 | 6.1  | 32 | 0.39 | 0.01 | 25.4 | 2.8 | 2.9 | 27 | 5.50 | | |
| 12 | 396 | 8.5  | 39 | 0.32 | 0.01 | 15.1 | 3.0 | 2.3 | 34 | 7.4  | | |
| 14 | 295 | 11.9 | 31 | 0.4  | 0.02 | 19.6 | 2.8 | 4.3 | 38 | 8.3  | | |
| 16 | 294 | 11.8 | ND | 0.4  | 0.01 | ND   | 2.0 | 4.6 | 34 | 10.7 | | |
| 24 | 552 | 16.1 | ND | 0.44 | 0.01 | ND   | 0   | 5.8 | 61 | 23.3 | | |

B Results for Non-Induced Culture

| Hr. After Growth Reached | Protein Conc. mg/L | | | hPTH Conc. mg/L | | | β-lactamase Activity U/L | | | β-galactosidase Activity U/L | | |
|---|---|---|---|---|---|---|---|---|---|---|---|---|
| at O.D.$_{600}$ = 0.3 | C | P | S | C | P | S | C | P | S | C | P | S |
| 6  | 99  | 6    | 23 | 6.4 | 0.05 | 5  | 20.2 | 79 | 58 | 4.5 | Not | |
| 12 | 285 | 7.5  | 20 | 4.4 | 0.1  | 10 | 39   | 20 | 75 | 2.7 | Detect- | |
| 24 | 564 | 18.7 | 31 | 1.9 | 0.02 | 17 | 7.4  | 47 | 96 | 2.2 | able | |

See Legends for descriptions of superscripts 1, 2, 3, 4, 5, 6 and 7 respectively.
Table 1 Legends
[1]Measured by the Bio-Rad protein assay using bovine serum albumin to provide the standard curve.
[2]Determined by radioimmunoassay N-tack kit (Incstar # 10412, Catalog # 96065).
[3]Assayed spectrophotometrically using nitrocefin as the substrate (Antimicrob. Ag. Chemother. Vol. 1, pp. 283–288, 1972). 1 U of β-galactosidase produces 1 nmol of nitrocefoic acid per min.
[4]Assayed according to Miller (Experiments in Molecular Genetics. Cold Spring Harbor Laboratory, cold Spring Harbor, NY, 1972). 1 U of β-galactosidase produces 1 nmol of o-nitrophenol per min.
[5]C stands for total cell lysate generated by sonication.
[6]P stands for periplasmic fraction generated by osmotic-shock technique (J. Biol. Chem. Vol. 241, pp. 3055–3062, 1966).
[7]S stands for culture supernatant.
ND: Not Determined.

Several significant findings are revealed in Table 1. Firstly, it is clear that PTH was excreted to the culture medium. That β-galactosidase was not detected in the culture medium indicates that the appearance of PTH in the

TABLE 2

Determination of Protein Concentration and Enzymatic Activities in Various Fractions of E. coli Culture Expressing hEGF

A Results for Induced Culture

| Hr. After IPTG Induction | Protein Conc.[1] mg/L | | | hEGF Conc.[2] mg/L | | | β-lactamase[3] Activity U/L | | | β-galactosidase[4] Activity U/L | | |
|---|---|---|---|---|---|---|---|---|---|---|---|---|
| at $O.D._{600} = 0.3$ | C[5] | P[6] | S[7] | C | P | S | C | P | S | C | P | S |
| 0 | 16 | 2 | 16 | 2 | 0 | 5 | 9.1 | 0.4 | 14.4 | 2.6 | Not | |
| 2 | 32 | 3 | 31 | 5 | 1 | 2 | 16.8 | 0.3 | 71 | 2.1 | Detect- | |
| 4 | 32 | 4 | 32 | 3.5 | 2 | 4 | 12.8 | 0.45 | 72 | 2.1 | able | |
| 6 | 85 | 4 | 32 | 3 | 0 | 30 | 13.5 | 0.42 | 80 | 2.9 | | |
| 8 | 140 | 5 | 28 | 2.5 | 0.5 | 27 | 13.7 | 0.37 | 79 | 6.2 | | |
| 10 | 285 | 6 | 25 | 2 | 0.5 | 32 | 7.6 | 0.33 | 77 | 2.0 | | |
| 12 | 224 | 6 | 27 | 3 | 0 | 29 | 7.4 | 0.4 | 81 | 1.1 | | |
| 14 | 272 | 5 | 25 | 3.5 | 0 | 28 | 6.5 | 0.52 | 78 | 2.3 | | |
| 16 | 413 | 8 | 27 | 3.5 | 0 | 23 | 5.7 | 0.55 | 82 | 0.6 | | |
| 24 | 362 | 11 | 32 | 2 | 0.5 | 33 | 1.1 | 1.1 | 72 | 13.3 | | |

B Results for Non-Induced Culture

| Hr. After Growth Reached | Protein Conc. mg/L | | | hEGF Conc. mg/L | | | β-lactamase Activity U/L | | | β-galactosidase[4] Activity U/L | | |
|---|---|---|---|---|---|---|---|---|---|---|---|---|
| at $O.D._{600} = 0.3$ | C | P | S | C | P | S | C | P | S | C | P | S |
| 6 | 105 | 14 | 21 | 17 | 0 | 13 | 39.8 | 19.6 | 5.8 | 0.52 | Not | |
| 12 | 144 | 9 | 35 | 15 | 2 | 23 | 34.9 | 9.5 | 19 | 0.52 | Detect- | |
| 24 | 144 | 20 | 60 | 10 | 0 | 90 | 6.3 | 0.8 | 32 | 3.7 | able | |

[2]Determined by radioimmunoassay kit (Amersham, Code 1M 1961).
See Legends to Table 1 for descriptions of superscripts 1, 3, 4, 5, 6 and 7 respectively.

The tabulated data reveals that EGF was excreted to the culture medium but not, as the β-galactosidase data shows, as a result of cell lysis. With induction by IPTG, EGF production at 4 hours was significant with maximum yields being realized about 10 hours after the culture reached mid-log phase. Again, the data reveals that IPTG induction is not essential. The absence of IPTG effect may result from the combined effect of the strong tac promoter and consensus ribosome binding site which is too strong to be counteracted by the lacI product which normally represses tac function. As a further observation, it will be noted that excretion of EGF from the periplasm is remarkably complete.

CD4:

E. coli strain JM 101 harbouring the CD4 excretion plasmid pcenATacCD4 was cultured in the same manner described above and induced with IPTG after the culture reached early log phase. Aliquots were taken at two hour intervals and the medium analyzed after dialysis, lyophilization and reconstitution in phosphate-buffered saline containing 0.02% NaN3 and 1 mM PMSF (an inhibitor of protease degradation). Samples were assayed for CD4 activity in a sandwich ELISA format using the commemially available anti-CD4 antibodies OKT4.2 as capture and OKT4-urease as conjugate. The results of the assay of the culture medium are tabulated below:

TABLE 3

Determination of CD4 Activity

| | O.D. 590 | |
|---|---|---|
| Hrs after induction | Culture Induction (30° C.) | Culture Induction (37° C.) |
| 2 | 0.218 | 0.226 |
| 4 | 0.377 | 0.335 |
| 6 | 0.268 | 0.229 |
| 8 | 0.316 | 0.218 |
| 10 | 0.247 | 0.276 |

*Values are corrected to reflect background (control - host/vector only).

It is significant to note that CD4 was excreted at both temperatures. At 30° C., the cenA product is not capable of leaking to any significant extent (see Guo et al., supra). Thus, the cenA product cannot reasonably be assumed to be responsible for CD4 leakage into the medium.

IL-6:

In preliminary experiments in which the culture medium of JM 101 transformants harbouring the IL-6 excretion plasmid were assayed, strongly positive assay results have been obtained. Specifically, 250 units of IL-6 activity/ml of medium were detected using the bioassay described by Koj et al, 1986, J. Immunol. Methods, 76, pp.317–327.

While the heterologous proteins produced by the respective plasmids exemplified above are unlikely to be "mature" in the sense that the N-terminus of the excreted protein is not authentic, it will be appreciated that these plasmids can be mutated site-specifically to remove DNA coding for superfluous N-terminal amino acid residues and allow the N-terminus of the mature protein to be fused directly with the C-terminus of the ompA signal peptide. Reference may be made to Kunkel et al, supra, for details on this procedure.

Systems useful for performing oligonucleotide-directed mutagenesis conducting site-specific mutagenesis are also sold commercially in kit form by Amersham International plc. In the specific case of the PTH excretion vector, pETacPTH, the mutagenesis technique can be employed to produce various forms of the PTH molecule fused directly to the ompA signal peptide when expressed i.e. PTH1-84, and PTH1-34.

EXAMPLE 4—Modification of Tac excretion vector

Figure 8:
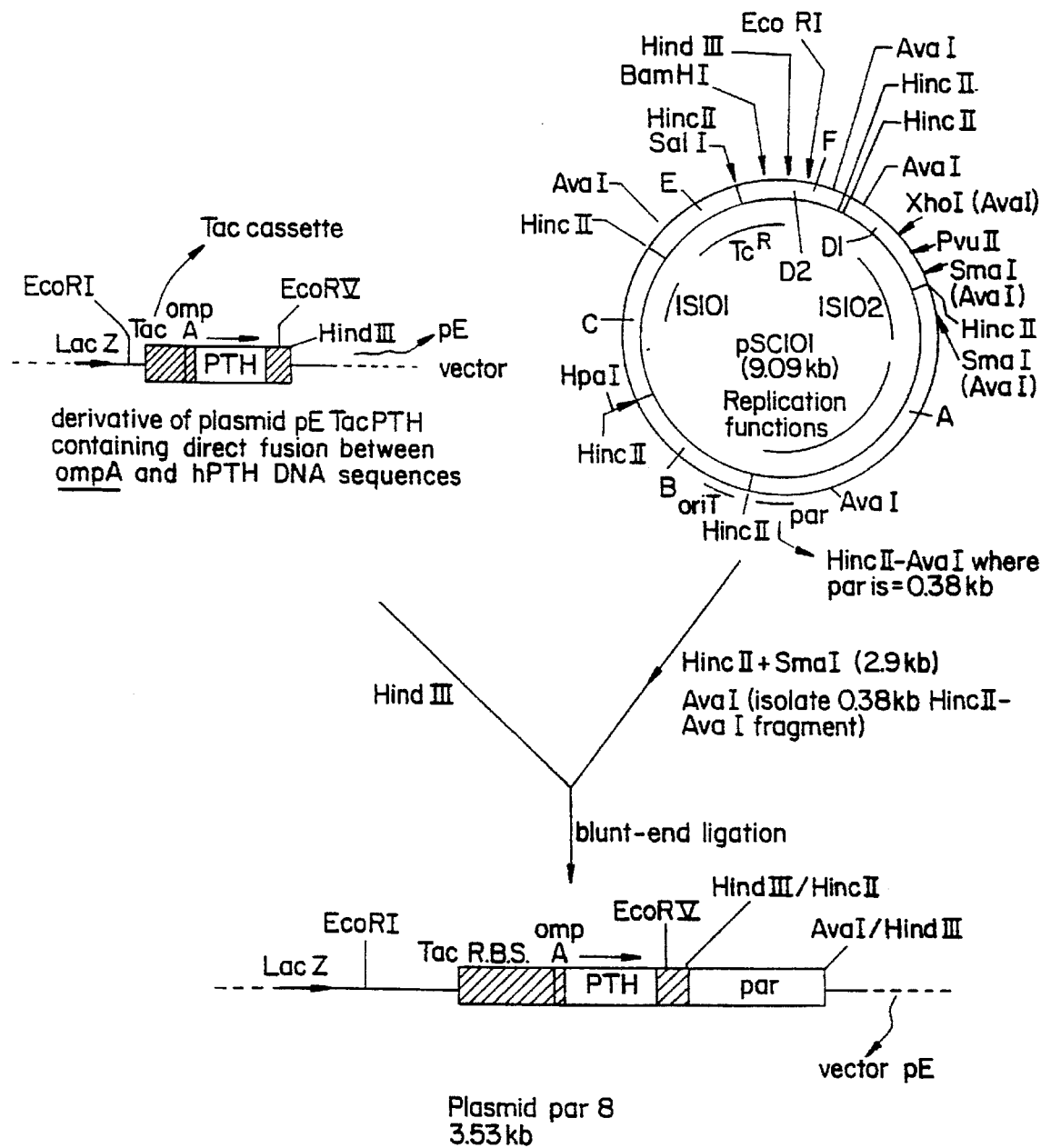
FIG. 8 illustrates schematically the incorporation of a 'par' element into a variant of pETacPTH.

A version of the pETacPTH plasmid, in which DNA coding for PTH1-84 had been brought, by site-specific mutagenesis, into direct fusion with DNA coding for the ompA signal was modified by incorporating thereon both the lacI$^q$ gene and a par element. To obtain the par element, E. coli plasmid pSC101 (Miller et al., supra) was cleaved with HincII and SmaI, thereby releasing a 2.9 kb fragment which was then cleaved by AvaI. The resulting 380 bp HincII/AvaI fragment harbouring the par element was then cloned, after gel purification, into the HindIII site immediately downstream of the Tac cassette, by blunt-end ligation. Construction of the resulting plasmid, designated par8, is illustrated in FIG. 8.

Figure 9:
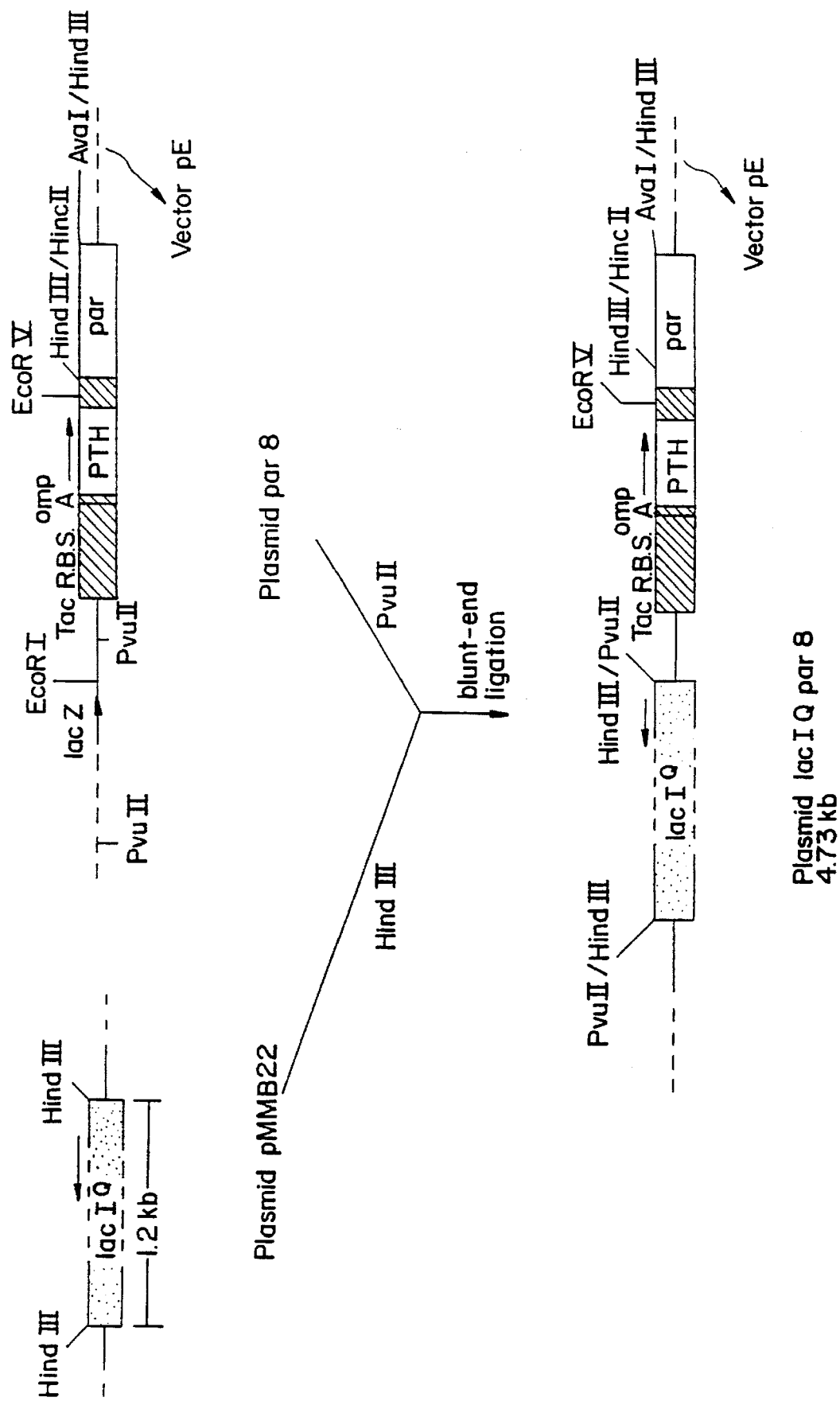
FIG. 9 illustrates schematically the incorporation of the lacI$^q$ gene into the par-containing variant of pETacPTH illustrated in FIG. 8.

The lacI$^q$ gene was then cloned into plasmid par8, using the strategy illustrated schematically in FIG. 9. To obtain the lacI$^q$ gene, the broad host range plasmid pMMB22 (described by Bagdasarian et al, supra) was cleaved with HindIII. A gel-purified 1.2 kb fragment harbouring the lacI$^q$ gene was then cloned, by blunt-end ligation, into PvuII-restricted plasmid par 8 i.e. incorporated upstream of the Tac cassette.

The performance of the resulting plasmid, which harbours the par element, the lacI$^q$ gene and the Tac/PTH cassette, was then evaluated in a variety of E. coli host strains. To assess performance of the lacI$^q$ component of the modified plasmid, wild type E. coli strains, lacking the lacI$^q$ genotype, were transformed. In all strains tested, including DH1, RR1, C600, CMK603 and EB505, bioactive PTH activity was detected following induction with IPTG, indicating that the product of the plasmid-encoded lacI$^q$ gene was functional. Functional par activity was also detected in JM101 transformants. Incorporation of the par element resulted in stable inheritance of the plasmid throughout many generations, even in the absence of selective pressure.

---

We claim:

1. A method for the production of a parathyroid hormone, comprising the steps of
 (a) obtaining a healthy *E. coli* bacterium with an excretion vector comprising
  (i) a coding region comprised of a first DNA that encodes the ompA signal peptide and a second DNA that encodes said parathyroid hormone, wherein said first DNA is linked in-frame to said second DNA;
  (ii) a control region comprised of a third DNA, said control region operably-linked to said coding region to enable expression of said parathyroid hormone, wherein said third DNA comprises the tac promoter, the lac operator, and a ribosome binding site, and
  (iii) a selection region comprised of a fourth DNA that encodes a second protein which, upon expression, imparts a selectable phenotype to said bacterium;
 (b) culturing said transformed *E. coli* bacterium in a suitable medium; and
 (c) recovering said parathyroid hormone from said medium without lysing said bacterium.

2. A method according to claim 1, wherein said heterologous protein is human PTH.

3. A method according to claim 1, wherein said vector further comprises a lacI$^q$ DNA derived from *Escherichia coli*.

4. A method according to claim 1, wherein said vector further comprises a par element DNA derived from *Escherichia coli*.

5. A method according to claim 1, wherein said vector further comprises a lacI$^q$ DNA and a par element DNA, both derived from *Escherichia coli*.

6. A method according to claim 5, wherein said vector further comprises a termination signal selected from the group consisting of the trpA, thr, his or phe terminators derived from *Escherichia coli*.

7. A method according to claim 5, wherein IPTG is added during said culturing.

8. A method according to claim 1, wherein said vector further comprises a termination signal selected from the group consisting of the trpA, thr, his or phe terminators derived from *Escherichia coli*.

9. A method according to claim 1, wherein said culturing takes place at 30° C.

10. A method according to claim 1, wherein said bacterium is *Escherichia coli* JM101.

11. A method according to claim 10, wherein said heterologous protein is human PTH.

12. A method according to claim 10, wherein said vector further comprises a lacI$^q$ DNA derived from *Escherichia coli*.

13. A method according to claim 10, wherein said vector further comprises a par element DNA derived from *Escherichia coli*.

14. A method according to claim 10, wherein said vector further comprises a lacI$^q$ DNA and a par element DNA, both derived from *Escherichia coli*.

15. A method according to claim 14, wherein said vector further comprises a termination signal selected from the group consisting of the trpA, thr, his or phe terminators derived from *Escherichia coli*.

16. A method according to claim 14, wherein IPTG is added during said culturing.

17. A method according to claim 10, wherein said vector further comprises a termination signal selected from the group consisting of the trpA, thr, his or phe terminators derived from *Escherichia coli*.

18. A method according to claim 10, wherein said culturing takes place at 30° C.

19. A method for obtaining a parathyroid hormone, comprising the steps of:
 (1) culturing, in a nutrient medium, an *E. coli* transformant obtained by transforming a healthy *E. coli* host strain with a secretion vector for directing secretion of said parathyroid hormone to the periplasm of said transformant; and
 (2) without lysing said transformant, recovering the parathyroid hormone from the medium in which said transformant has been cultured.

20. The method of claim 19, wherein the parathyroid hormone is human parathyroid hormone.

* * * * *